(12) United States Patent
Kumar

(10) Patent No.: US 12,036,113 B2
(45) Date of Patent: Jul. 16, 2024

(54) DELIVERY OF HEART CHAMBER PROSTHETIC VALVE IMPLANT

(71) Applicant: 4C Medical Technologies, Inc., Brooklyn Park, MN (US)

(72) Inventor: Saravana B. Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 0 days.

(21) Appl. No.: 16/007,630

(22) Filed: Jun. 13, 2018

(65) Prior Publication Data

US 2018/0360602 A1 Dec. 20, 2018

Related U.S. Application Data

(60) Provisional application No. 62/519,576, filed on Jun. 14, 2017.

(51) Int. Cl.
*A61F 2/24* (2006.01)

(52) U.S. Cl.
CPC .......... *A61F 2/2418* (2013.01); *A61F 2/2427* (2013.01)

(58) Field of Classification Search
CPC ...... A61F 2/2418; A61F 2/2427; A61F 2/243; A61F 2/246; A61F 2/2466; A61F 2/2469
See application file for complete search history.

(56) References Cited

U.S. PATENT DOCUMENTS

| | | |
|---|---|---|
| 4,424,833 A | 1/1984 | Spector |
| 4,503,569 A | 3/1985 | Dotter |
| 4,733,665 A | 3/1988 | Palmaz |
| 4,878,906 A | 11/1989 | Lindemann |
| 5,190,528 A | 3/1993 | Fonger |
| 5,415,667 A | 5/1995 | Frater |

(Continued)

FOREIGN PATENT DOCUMENTS

| | | |
|---|---|---|
| AU | 2014203064 B2 | 6/2015 |
| AU | 2015230879 A1 | 10/2015 |

(Continued)

OTHER PUBLICATIONS

International Search Report and Written Opinion, dated Aug. 30, 2018, for PCT Application No. PCT/US18/37536, filed Jun. 14, 2018.

(Continued)

*Primary Examiner* — Richard G Louis

(74) *Attorney, Agent, or Firm* — Weiss & Arons LLP

(57) ABSTRACT

The invention relates to prosthetic heart valves comprising a stent frame with valve support disposed or inverted at least partially within the stent frame, wherein the valve support is at least partially within the interior of the stent frame. The inverted configuration comprises a maximum number of layers of material in cross section where the stent frame and valve support overlap. The maximum number of cross-sectional layers of material structure may be reduced to, e.g., two layers of material to reduce outer diameter during delivery by everting the valve portion to a position located outside of the stent portion, followed by inverted reconfiguration back to the inverted anchoring structure after delivery from the lumen of the delivery catheter to the heart chamber.

23 Claims, 1 Drawing Sheet

(56) References Cited

U.S. PATENT DOCUMENTS

| | | |
|---|---|---|
| 5,441,483 A | 8/1995 | Avitall |
| 5,693,083 A | 12/1997 | Baker |
| 5,693,089 A | 12/1997 | Inoue |
| 5,776,188 A | 7/1998 | Shepherd |
| 5,843,090 A | 12/1998 | Schuetz |
| 5,928,258 A | 7/1999 | Khan |
| 5,957,949 A | 9/1999 | Leonhardt |
| 5,968,070 A | 10/1999 | Bley |
| 6,123,723 A | 9/2000 | Konya |
| 6,152,144 A | 11/2000 | Lesh |
| 6,231,602 B1 | 5/2001 | Carpentier |
| 6,287,334 B1 | 9/2001 | Moll |
| 6,319,280 B1 | 11/2001 | Schoon |
| 6,319,281 B1 | 11/2001 | Patel |
| 6,332,893 B1 | 12/2001 | Mortier |
| 6,371,983 B1 | 4/2002 | Lane |
| 6,409,758 B2 | 6/2002 | Stobie |
| 6,425,916 B1 | 7/2002 | Garrison |
| 6,471,718 B1 | 10/2002 | Staehle |
| 6,494,909 B2 | 12/2002 | Greenhalgh |
| 6,503,272 B2 | 1/2003 | Duerig |
| 6,540,782 B1 | 4/2003 | Snyders |
| 6,569,196 B1 | 5/2003 | Vesely |
| 6,589,275 B1 | 7/2003 | Ivancev |
| 6,702,826 B2 | 3/2004 | Liddicoat |
| 6,738,655 B1 | 5/2004 | Sen |
| 6,790,231 B2 | 9/2004 | Liddicoat |
| 6,790,237 B2 | 9/2004 | Stinson |
| 6,821,297 B2 | 11/2004 | Snyders |
| 6,830,585 B1 | 12/2004 | Artof |
| 6,840,957 B2 | 1/2005 | Dimatteo |
| 6,875,231 B2 | 4/2005 | Anduiza |
| 7,011,671 B2 | 3/2006 | Welch |
| 7,041,132 B2 | 5/2006 | Quijano |
| 7,044,966 B2 | 5/2006 | Svanidze |
| 7,125,420 B2 | 10/2006 | Rourke |
| 7,153,324 B2 | 12/2006 | Case |
| 7,252,682 B2 | 8/2007 | Seguin |
| 7,276,077 B2 | 10/2007 | Zadno-Azizi |
| 7,276,078 B2 | 10/2007 | Spenser |
| 7,291,168 B2 | 11/2007 | Macoviak |
| 7,364,588 B2 | 4/2008 | Mathis |
| 7,381,220 B2 | 6/2008 | Macoviak |
| 7,442,204 B2 | 10/2008 | Schwammenthal |
| 7,445,631 B2 | 11/2008 | Salahieh |
| 7,455,689 B2 | 11/2008 | Johnson |
| 7,510,572 B2 | 3/2009 | Gabbay |
| 7,524,331 B2 | 4/2009 | Birdsall |
| 7,611,534 B2 | 11/2009 | Kapadia |
| 7,704,277 B2 | 4/2010 | Zakay |
| 7,749,266 B2 | 7/2010 | Forster |
| 7,758,491 B2 | 7/2010 | Buckner |
| 7,780,723 B2 | 8/2010 | Taylor |
| 7,789,909 B2 | 9/2010 | Andersen |
| 7,935,144 B2 | 5/2011 | Robin |
| 7,959,672 B2 | 6/2011 | Salahieh |
| 7,998,196 B2 | 8/2011 | Mathison |
| 8,012,201 B2 | 9/2011 | Lashinski |
| 8,016,877 B2 | 9/2011 | Seguin |
| 8,021,420 B2 | 9/2011 | Dolan |
| 8,029,556 B2 | 10/2011 | Rowe |
| D648,854 S | 11/2011 | Braido |
| 8,052,592 B2 | 11/2011 | Goldfarb |
| 8,057,493 B2 | 11/2011 | Goldfarb |
| 8,070,802 B2 | 12/2011 | Lamphere |
| 8,083,793 B2 | 12/2011 | Lane |
| D653,341 S | 1/2012 | Braido |
| D653,342 S | 1/2012 | Braido |
| 8,092,524 B2 | 1/2012 | Nugent |
| 8,142,492 B2 | 3/2012 | Forster |
| 8,147,541 B2 | 4/2012 | Forster |
| D660,433 S | 5/2012 | Braido |
| D660,967 S | 5/2012 | Braido |
| 8,167,932 B2 | 5/2012 | Bourang |
| 8,236,049 B2 | 8/2012 | Rowe |
| 8,246,677 B2 | 8/2012 | Ryan |
| 8,252,051 B2 | 8/2012 | Chau |
| 8,287,538 B2 | 10/2012 | Brenzel et al. |
| 8,308,798 B2 | 11/2012 | Pintor |
| 8,313,525 B2 | 11/2012 | Tuval et al. |
| 8,348,998 B2 | 1/2013 | Pintor |
| 8,348,999 B2 | 1/2013 | Kheradvar |
| 8,366,768 B2 | 2/2013 | Zhang |
| 8,398,708 B2 | 3/2013 | Meiri |
| 8,409,275 B2 | 4/2013 | Matheny |
| 8,414,644 B2 | 4/2013 | Quadri |
| 8,414,645 B2 | 4/2013 | Dwork |
| 8,439,970 B2 | 5/2013 | Jimenez |
| 8,454,686 B2 | 6/2013 | Alkhatib |
| 8,465,541 B2 | 6/2013 | Dwork |
| 8,491,650 B2 | 7/2013 | Wiemeyer |
| 8,512,400 B2 | 8/2013 | Tran |
| 8,518,106 B2 | 8/2013 | Duffy |
| 8,535,373 B2 | 9/2013 | Stacchino |
| 8,562,673 B2 | 10/2013 | Yeung |
| 8,568,472 B2 | 10/2013 | Marchand |
| 8,579,963 B2 | 11/2013 | Tabor |
| 8,579,964 B2 | 11/2013 | Lane |
| 8,603,159 B2 | 12/2013 | Seguin |
| 8,623,075 B2 | 1/2014 | Murray, III |
| 8,636,764 B2 | 1/2014 | Miles |
| 8,641,757 B2 | 2/2014 | Pintor |
| 8,657,870 B2 | 2/2014 | Turovskiy |
| 8,663,318 B2 | 3/2014 | Ho |
| 8,679,176 B2 | 3/2014 | Matheny |
| 8,721,715 B2 | 5/2014 | Wang |
| 8,740,976 B2 | 6/2014 | Tran |
| 8,747,459 B2 | 6/2014 | Nguyen |
| 8,747,461 B2 | 6/2014 | Centola |
| 8,764,793 B2 | 7/2014 | Lee |
| 8,764,820 B2 | 7/2014 | Dehdashtian |
| 8,778,020 B2 | 7/2014 | Gregg |
| 8,790,396 B2 | 7/2014 | Bergheim |
| 8,795,357 B2 | 8/2014 | Yohanan |
| 8,805,466 B2 | 8/2014 | Salahieh |
| 8,814,931 B2 | 8/2014 | Wang |
| 8,828,043 B2 | 9/2014 | Chambers |
| 8,828,051 B2 | 9/2014 | Javois |
| 8,845,711 B2 | 9/2014 | Miles |
| 8,845,722 B2 | 9/2014 | Gabbay |
| 8,852,271 B2 | 10/2014 | Murray, III |
| 8,852,272 B2 | 10/2014 | Gross |
| 8,870,949 B2 | 10/2014 | Rowe |
| 8,876,897 B2 | 11/2014 | Kheradvar |
| 8,906,022 B2 | 12/2014 | Krinke et al. |
| 8,926,692 B2 | 1/2015 | Dwork |
| 8,956,402 B2 | 2/2015 | Cohn |
| 8,956,405 B2 | 2/2015 | Wang |
| 8,961,518 B2 | 2/2015 | Kyle et al. |
| 8,986,372 B2 | 3/2015 | Murry, III |
| 8,986,374 B2 | 3/2015 | Cao |
| 8,986,375 B2 | 3/2015 | Garde |
| 8,998,980 B2 | 4/2015 | Shipley |
| 8,998,982 B2 | 4/2015 | Richter |
| 9,005,273 B2 | 4/2015 | Salahieh |
| 9,011,527 B2 | 4/2015 | Li |
| D730,520 S | 5/2015 | Braido |
| D730,521 S | 5/2015 | Braido |
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |
| 9,138,313 B2 | 9/2015 | McGuckin, Jr. |
| 9,144,493 B2 | 9/2015 | Carr |
| 9,144,494 B2 | 9/2015 | Murray |
| 9,155,619 B2 | 10/2015 | Liu |

(56) References Cited

U.S. PATENT DOCUMENTS

| | | |
|---|---|---|
| 9,161,835 B2 | 10/2015 | Rankin |
| 9,173,737 B2 | 11/2015 | Hill |
| 9,192,466 B2 | 11/2015 | Kovalsky |
| 9,226,820 B2 | 1/2016 | Braido |
| 9,232,942 B2 | 1/2016 | Seguin |
| 9,232,996 B2 | 1/2016 | Sun |
| 9,248,016 B2 | 2/2016 | Oba |
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr. |
| 9,439,763 B2 | 9/2016 | Geist |
| 9,439,795 B2 | 9/2016 | Wang |
| 9,480,560 B2 | 11/2016 | Quadri |
| 9,498,370 B2 | 11/2016 | Kyle et al. |
| 9,504,569 B2 | 11/2016 | Malewicz |
| 9,522,062 B2 | 12/2016 | Tuval |
| 9,566,152 B2 | 2/2017 | Schweich, Jr. |
| 9,579,194 B2 | 2/2017 | Elizondo |
| 9,579,197 B2 | 2/2017 | Duffy |
| 9,622,863 B2 | 4/2017 | Karapetian |
| 9,717,592 B2 | 8/2017 | Thapliyal |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola et al. |
| 9,839,765 B2 | 12/2017 | Morris |
| 9,861,477 B2 | 1/2018 | Backus |
| 9,872,765 B2 | 1/2018 | Zeng |
| 9,877,830 B2 | 1/2018 | Lim |
| 9,968,443 B2 | 5/2018 | Bruchman |
| 10,004,601 B2 | 6/2018 | Tuval |
| 10,016,274 B2 | 7/2018 | Tabor |
| 10,016,275 B2 | 7/2018 | Nyuli |
| 10,022,132 B2 | 7/2018 | Wlodarski et al. |
| 10,034,750 B2 | 7/2018 | Morriss |
| 10,039,637 B2 | 8/2018 | Maimon |
| 10,039,642 B2 | 8/2018 | Hillukka |
| 10,098,735 B2 | 10/2018 | Lei |
| 10,098,763 B2 | 10/2018 | Lei |
| 10,117,742 B2 | 11/2018 | Braido |
| 10,143,551 B2 | 12/2018 | Braido |
| 10,182,907 B2 | 1/2019 | Lapeyre |
| 10,195,023 B2 | 2/2019 | Wrobel |
| 10,226,340 B2 | 3/2019 | Keren |
| 10,231,834 B2 | 3/2019 | Keidar |
| 10,238,490 B2 | 3/2019 | Gifford, III |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,376,363 B2 | 8/2019 | Quadri |
| 10,383,725 B2 | 8/2019 | Chambers |
| 10,390,943 B2 | 8/2019 | Hernandez |
| 10,405,974 B2 | 9/2019 | Hayes |
| 10,433,961 B2 | 10/2019 | McLean |
| 10,470,880 B2 | 11/2019 | Braido |
| 10,492,907 B2 | 12/2019 | Duffy |
| 10,500,041 B2 | 12/2019 | Valdez |
| 10,507,107 B2 | 12/2019 | Nathe |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,524,910 B2 | 1/2020 | Hammer |
| 10,531,951 B2 | 1/2020 | Spargias |
| 10,537,427 B2 | 1/2020 | Zeng |
| 10,555,809 B2 | 2/2020 | Hastings |
| 10,555,812 B2 | 2/2020 | Duffy |
| 10,561,495 B2 | 2/2020 | Chambers |
| 10,595,992 B2 | 3/2020 | Chambers |
| 10,610,362 B2 | 4/2020 | Quadri |
| 10,653,523 B2 | 5/2020 | Chambers |
| 10,667,905 B2 | 6/2020 | Ekvall |
| 10,667,909 B2 | 6/2020 | Richter |
| 10,702,379 B2 | 7/2020 | Garde |
| 10,702,380 B2 | 7/2020 | Morriss |
| 10,709,560 B2 | 7/2020 | Kofidis |
| 10,751,169 B2 | 8/2020 | Chambers |
| 10,751,170 B2 | 8/2020 | Richter |
| 10,751,172 B2 | 8/2020 | Para |
| 10,758,265 B2 | 9/2020 | Siegel |
| 10,758,342 B2 | 9/2020 | Chau |
| 10,779,935 B2 | 9/2020 | Scorsin |
| 10,779,936 B2 | 9/2020 | Pollak |
| 10,779,968 B2 | 9/2020 | Giasolli |
| 10,786,351 B2 | 9/2020 | Christianson |
| 10,828,152 B2 | 11/2020 | Chambers |
| 10,856,983 B2 | 12/2020 | Keränen |
| 10,869,756 B2 | 12/2020 | Al-Jilaihawi |
| 10,874,513 B2 | 12/2020 | Chambers |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,007,054 B2 | 5/2021 | Braido |
| 11,013,599 B2 | 5/2021 | Subramanian |
| 11,026,782 B2 | 6/2021 | Chambers |
| 11,026,788 B2 | 6/2021 | Metchik et al. |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,096,781 B2 | 8/2021 | Gurovich |
| 11,147,666 B2 | 10/2021 | Braido |
| 11,154,239 B2 | 10/2021 | Toth |
| 11,154,396 B2 | 10/2021 | Dibie |
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |
| 11,278,406 B2 | 3/2022 | Straubinger |
| 11,351,028 B2 | 6/2022 | Peterson |
| 11,389,293 B2 | 7/2022 | Torrianni |
| 11,395,734 B2 | 7/2022 | Lee |
| 11,413,141 B2 | 8/2022 | Morin |
| 11,419,716 B2 | 8/2022 | Braido |
| 11,452,628 B2 | 9/2022 | Diedering |
| 11,458,013 B2 | 10/2022 | Righini |
| 2001/0005787 A1* | 6/2001 | Oz ............... A61B 17/064 606/142 |

(56) References Cited

U.S. PATENT DOCUMENTS

| | | |
|---|---|---|
| 2002/0072710 A1 | 6/2002 | Stewart |
| 2002/0161377 A1 | 10/2002 | Rabkin |
| 2003/0057156 A1 | 3/2003 | Peterson |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0137622 A1 | 6/2005 | Griffin |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado, III |
| 2006/0276874 A1 | 12/2006 | Wilson |
| 2007/0016288 A1 | 1/2007 | Gurskis |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2008/0300678 A1 | 12/2008 | Eidenschink et al. |
| 2009/0076585 A1 | 3/2009 | Hendriksen |
| 2009/0082840 A1* | 3/2009 | Rusk .............. A61F 2/89 623/1.11 |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0218619 A1* | 9/2011 | Benichou .............. A61F 2/2412 623/2.11 |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0065728 A1* | 3/2012 | Gainor ................. A61F 2/2445 623/2.11 |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197193 A1 | 8/2012 | Krolik et al. |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031924 A1 | 1/2014 | Bruchman et al. |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |

(56) References Cited

U.S. PATENT DOCUMENTS

| | | |
|---|---|---|
| 2014/0088696 A1 | 3/2014 | Figulla |
| 2014/0114340 A1 | 4/2014 | Zhou |
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramani |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | McNamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1* | 11/2015 | Levi ............... A61F 2/2427 623/2.11 |
| 2015/0327995 A1 | 11/2015 | Morin |
| 2015/0327996 A1 | 11/2015 | Fahim |
| 2015/0327999 A1 | 11/2015 | Board |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |

(56) References Cited

U.S. PATENT DOCUMENTS

| | | |
|---|---|---|
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | McCann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor et al. |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | McKinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramanian |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein et al. |
| 2016/0235530 A1 | 8/2016 | Thomas |
| 2016/0235531 A1 | 8/2016 | Ciobanu |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331529 A1 | 11/2016 | Marchand |
| 2016/0346081 A1 | 12/2016 | Zeng |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson et al. |
| 2017/0079790 A1 | 3/2017 | Vidlund |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0252191 A1 | 9/2017 | Pacetti |
| 2017/0281193 A1 | 10/2017 | Asirvatham |
| 2017/0333102 A1 | 11/2017 | Peterson et al. |
| 2017/0348098 A1 | 12/2017 | Rowe |
| 2017/0360570 A1 | 12/2017 | Berndt et al. |
| 2018/0014830 A1 | 1/2018 | Neumann |
| 2018/0055629 A1 | 3/2018 | Oba et al. |
| 2018/0092744 A1 | 4/2018 | Von Oepen |
| 2018/0116843 A1 | 5/2018 | Schreck |
| 2018/0116848 A1 | 5/2018 | McHugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0224028 A1 | 7/2019 | Finn |
| 2019/0247189 A1 | 8/2019 | Dale |
| 2019/0321530 A1 | 10/2019 | Cambronne |
| 2019/0321531 A1 | 10/2019 | Cambronne |
| 2019/0365534 A1* | 12/2019 | Kramer ............... A61F 2/2418 |
| 2019/0365538 A1 | 12/2019 | Chambers |
| 2020/0000592 A1* | 1/2020 | Lee ............... A61F 2/2463 |
| 2020/0030088 A1 | 1/2020 | Vidlund |
| 2020/0069423 A1 | 3/2020 | Peterson |
| 2020/0069449 A1 | 3/2020 | Diedering |
| 2020/0100897 A1 | 4/2020 | McLean |
| 2020/0113682 A1 | 4/2020 | Chang |
| 2020/0113719 A1 | 4/2020 | Desrosiers et al. |
| 2020/0129294 A1 | 4/2020 | Hariton |
| 2020/0155306 A1 | 5/2020 | Bonyuet |
| 2020/0163765 A1 | 5/2020 | Christianson |
| 2020/0179115 A1 | 6/2020 | Chambers |
| 2020/0188101 A1 | 6/2020 | Chambers |
| 2020/0222179 A1 | 7/2020 | Chambers |
| 2020/0253733 A1 | 8/2020 | Subramanian |
| 2020/0261219 A1 | 8/2020 | Kumar |
| 2020/0276013 A1 | 9/2020 | Chambers |
| 2020/0315678 A1 | 10/2020 | Mazzio et al. |
| 2020/0337765 A1 | 10/2020 | Smith |
| 2020/0368023 A1 | 11/2020 | Kheradvar |
| 2020/0375733 A1 | 12/2020 | Diedering |
| 2021/0236274 A1 | 8/2021 | Benson et al. |
| 2021/0236276 A1 | 8/2021 | Diedering |
| 2021/0275297 A1 | 9/2021 | Berndt |

(56) References Cited

U.S. PATENT DOCUMENTS

| | | | |
|---|---|---|---|
| 2021/0275301 A1 | 9/2021 | Kumar | |
| 2021/0290383 A1 | 9/2021 | Chambers | |
| 2022/0031451 A1 | 2/2022 | Spence | |
| 2022/0338979 A1 | 10/2022 | Benichou | |
| 2023/0218397 A1 | 7/2023 | Chambers et al. | |
| 2023/0372089 A1 | 11/2023 | Kumar | |

FOREIGN PATENT DOCUMENTS

| | | |
|---|---|---|
| AU | 2013201970 B2 | 3/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 201870772 U | 6/2011 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 107252363 B | 4/2020 |
| CN | 106913909 B | 9/2020 |
| CN | 107007887 B | 10/2020 |
| DE | 102010021345 A1 | 11/2011 |
| EP | 2596754 A1 | 5/2013 |
| EP | 2967858 A2 | 1/2016 |
| EP | 2982336 A1 | 2/2016 |
| EP | 2967845 B1 | 8/2018 |
| EP | 2950752 B1 | 7/2022 |
| JP | 2016531722 A | 10/2016 |
| WO | WO1995016476 A1 | 6/1995 |
| WO | WO2009127973 A2 | 10/2009 |
| WO | WO2014210299 A1 | 12/2014 |
| WO | WO2015004173 A1 | 1/2015 |
| WO | WO2016100806 A1 | 6/2016 |
| WO | 2016126942 | 8/2016 |
| WO | WO2019006387 | 1/2019 |

OTHER PUBLICATIONS

International Preliminary Report on Patentability dated Dec. 17, 2019 for PCT/US2018/037536, filed Jun. 14, 2018.
Supplementary European Search Report and Written Opinion issued by the EPO in application No. 18816952, dated Jan. 26, 2021.
Japanese Office Action in Application No. 2019-569834, May 15, 2023.
Chinese Office Action in Application No. 201880040116.4, Jul. 6, 2021.
Chinese Office Action in Application No. 201880040116.4, Feb. 18, 2022.
Chinese Office Action in Application No. 201880040116.4, Oct. 10, 2022.
Chinese Rejection Decision in Application No. 201880040116.4, Feb. 25, 2023.
European Office Action in Application No. 18816952.8, Jan. 26, 2021.
Indian Examination Report in Application No. 201937052443, Feb. 28, 2022.
Japanese Office Action in Application No. 2019-569834, Jul. 27, 2022.
Reed Miller, Start-Up Spotlight: 4C Addresses Mitral Regurgitation with Unique 'Dome' Device, https:/medtech.citeline.com/MT105076/StartUp-Spotlight-4C-Addresses-Mitral-Regurgitation-With-Unique-Dome-Device Published by Citeline on Jun. 29, 2017.
A Novel Transcatheter Mitral Valve Replacement System, Dr. Phillippe Genereux, MD, Jun. 14, 2017.

* cited by examiner

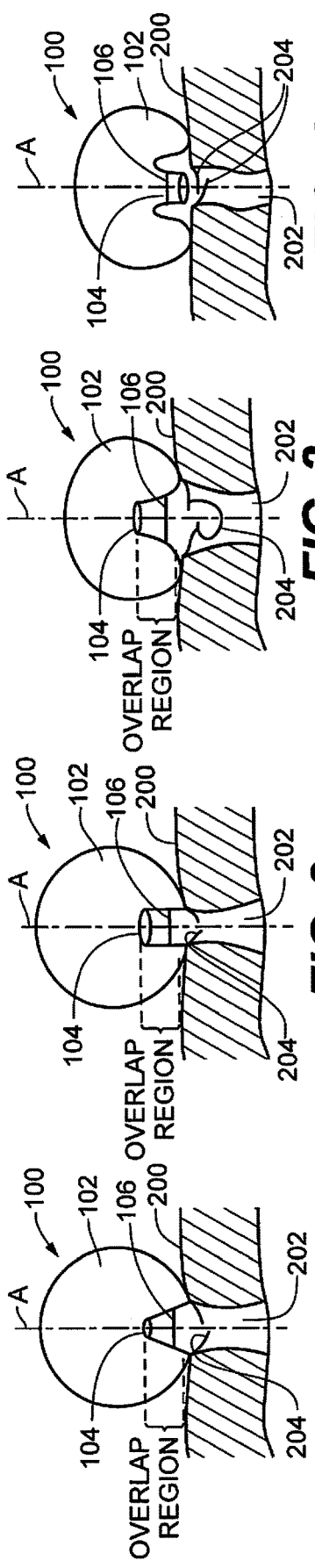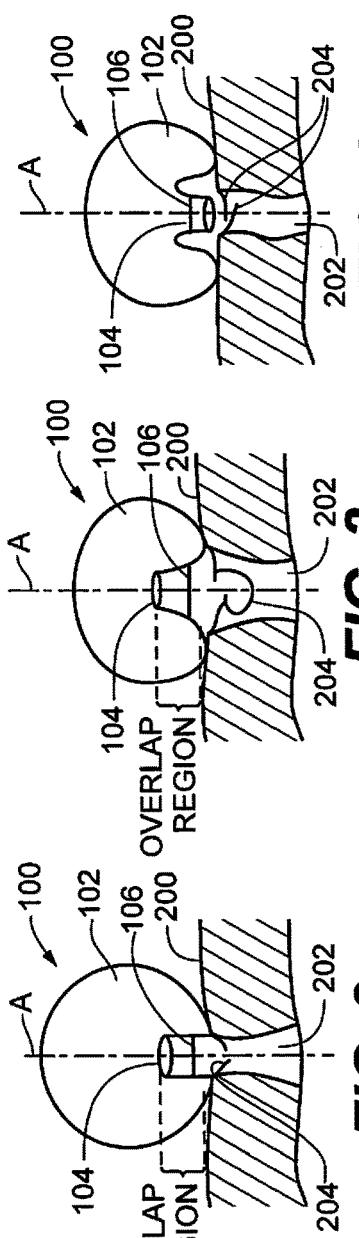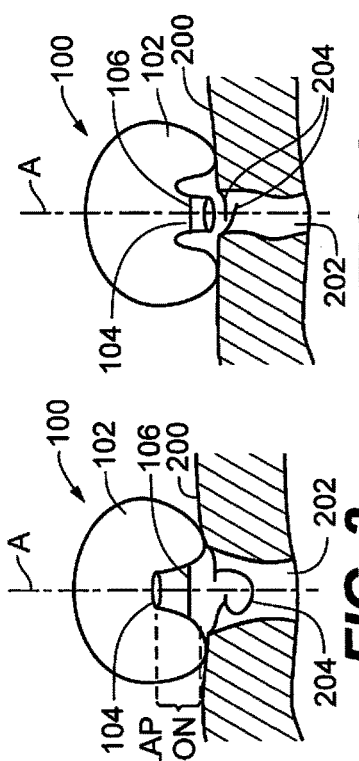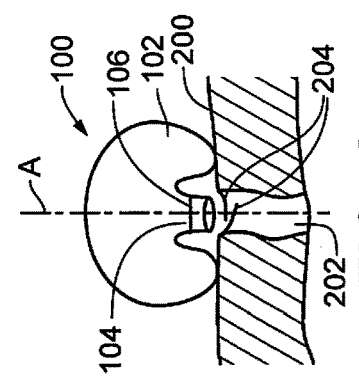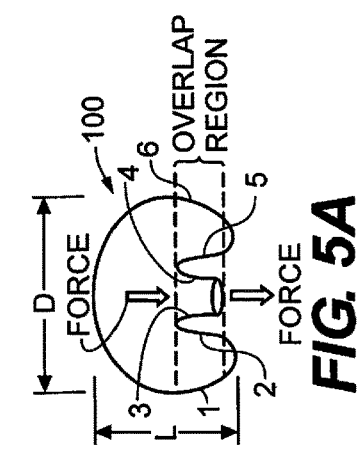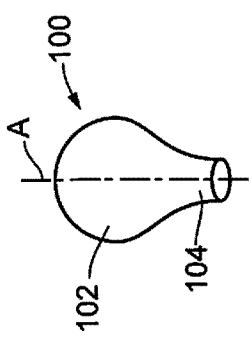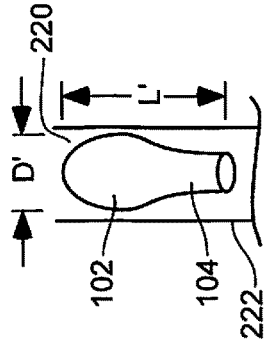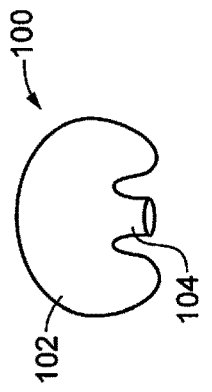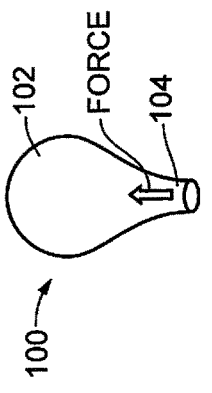

DELIVERY OF HEART CHAMBER PROSTHETIC VALVE IMPLANT

CROSS-REFERENCE TO RELATED APPLICATIONS

This application claims the benefit of U.S. Provisional Application Ser. No. 62/519,576, filed Jun. 14, 2017, and titled DELIVERY OF HEART CHAMBER PROSTHETIC VALVE IMPLANT, the entire contents of which are incorporated herein by reference.

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber. More specifically, the invention relates to preferably single-chamber anchoring frames comprising generally a stent portion and a valve portion disposed or inverted at least partially within the stent portion in the inverted, deployed configuration, wherein the inverted valve portion overlaps with at least a portion of the stent portion. The deployed configuration thus comprises a number of layers of material, most preferably more than two layers, along at least a portion of the anchoring frame in cross-section and may include two layers for the stent frame portion and two layers for the valve support portion. The cross-sectional layers of material structure may be reduced to, e.g., two layers of material to reduce outer diameter during delivery by everting the valve portion to a position located outside of the stent portion, followed by inverted reconfiguration back to the anchoring structure with more than two layers in cross section after delivery from the lumen of the delivery catheter and in preparation for implantation.

Description of the Related Art

Prosthetic cardiac valve and left atrial appendage occluding devices are well known in the art. The native heart valves, e.g., aortic, pulmonary, tricuspid and mitral valves, are critical in assuring the forward-only flow of an adequate supply of blood through the cardiovascular system. These heart valves may lose functionality as a result of, inter alia, congenital, inflammatory, infectious diseases or conditions. Early interventions repaired or replaced the dysfunctional valve(s) during open heart surgery. More recently, besides the open heart surgical approach discussed above, gaining access to the valve of interest may be achieved percutaneously via one of at least the following known access routes: transapical; transfemoral; transatrial; and transseptal delivery techniques, collectively transcatheter techniques.

Generally, in a transcatheter technique, the prosthetic valve is mounted within a stented frame that is capable of achieving collapsed and expanded states. The device is collapsed and advanced through a sheath or delivery catheter positioned in a blood vessel of the patient until reaching the implantation site. The stented frame is generally released from the catheter or sheath and, by a variety of means, expanded with the valve to the expanded functional size and orientation within the heart. One of the key issues is ease of delivery of the prosthetic valve, including the stent frame and valve. More specifically the outer diameter of the collapsed device within the catheter is of significant interest. The present invention addresses this issue.

BRIEF DESCRIPTION OF THE SEVERAL VIEWS OF THE DRAWINGS

FIG. 1 illustrates a cross-sectional view of one embodiment of the present invention.

FIG. 2 illustrates a cross-sectional view of one embodiment of the present invention.

FIG. 3 illustrates a cross-sectional view of one embodiment of the present invention.

FIG. 4 illustrates a cross-sectional view of one embodiment of the present invention.

FIG. 5A illustrates a cross-sectional view of one embodiment of the present invention.

FIG. 5B illustrates a cross-sectional view of one embodiment of the present invention.

FIG. 5C illustrates a cross-sectional and partial cutaway view of one embodiment of the present invention.

FIG. 5D illustrates a cross-sectional view of one embodiment of the present invention.

FIG. 5E illustrates a cross-sectional view of one embodiment of the present invention.

DETAILED DESCRIPTION OF THE INVENTION

Generally, the prosthetic heart valve comprises a collapsible and expandable stent frame as is commonly known in the art and that may be partially manufactured from a shape memory alloy to facilitate biased expansion, and an internally supported one-way valve. The stent frame comprises a lower aperture and is provided with a valve support substantially surrounding the lower aperture and that comprises a first inverted deployed position inside the stent frame and a second everted delivery position outside the stent frame. The stent frame may comprise a central longitudinal axis that the valve support is generally centered around and along which the valve support may translate to achieve the first inverted and second everted positions. The translation from the first inverted position to the second inverted position, and from the second inverted position to the first inverted position occurs by enabling the valve support to move through the lower aperture. The operative connection of the valve support with the stent frame allows flexion, stretching or hinging movement of the valve support relative to the stent frame to achieve the first inverted and second everted positions. Such flexing, stretching and/or hinging connections may be achieved by the expansion and/or collapse of stent frame cells and are well known to the skilled artisan. Therefore, the stent frame and valve support may comprise a stented structure, wherein the stent frame and valve support comprise stent cells and wherein the valve support may be formed from the same material as the stented structure, wherein the valve support structure is turned inside, or inverted within, the interior of the stent frame.

The valve support may be a cylinder with a height and inner and outer diameters that may be constant or that may vary over the height of the cylinder as in FIG. 2, for example. Alternatively, the valve support may comprise a cone-shaped structure as shown in FIG. 1. The valve support may comprise a separately manufactured structure that is operatively connected with the stent frame. Alternatively, the valve support may be formed from the same continuous layer that forms the stent frame, wherein the valve support is inverted within the stent frame in a deployed configuration. The term "operatively engaged" or "operative engagement" relating to the relationship of the valve support and the frame is defined herein to cover both of these possible arrangements. In each embodiment, the valve support is adapted and configured to transition between an inverted position at least partially within the interior of the stent frame and an everted position wherein the valve support is located outside of the stent frame.

The illustrated cone-shaped structure comprises side walls of non-constant diameter wherein the diameter increases from the top of the valve support to the bottom. Such a cone-shaped valve support may also comprise side walls of substantially constant diameter. Still more alternatively, the valve support may comprise other shaping geometries and/or dimensions. What is minimally required is that the valve support be in operative engagement and connection with the frame and valve and amenable to achieving the first inverted and second everted positions. The walls of the valve support must be sufficiently flexible or compliant to enable the valve support to translate through and/or within the lower orifice to achieve the first inverted, deployed position and/or second everted, delivery position. A flexible polymer or mesh or slidable metal frame construction, or similar may be used, as will be well known to the skilled artisan. In addition, the material may be constructed from a laser cut, wire or braided construction of a self-expandable material.

It is noteworthy that the valve support may be at least partially within the interior of the stent frame when deployed in the first inverted position. In other embodiments, the valve support may be entirely within the stent frame when deployed in the first inverted position. Stated differently, the valve support may at least partially overlap with the stent frame within an overlap region as discussed further below.

Further, the position of the valve as supported by the valve support, once deployed in an exemplary left atrium for supplementing and/or replacing the function of native mitral valve leaflets, the left atrium further comprising an upper annular surface or annular plane and an annulus, may be: (1) collinear with the upper annular plane or surface; (2) may be within the annulus or annular throat, i.e., below the upper annular plane or surface; or (3) above the annular plane or surface.

The prosthetic heart valve may in some embodiments be biased towards achieving the first inverted position and may, for example, be subject to a biasing expanding force that urges the valve support to the first inverted position. The biasing expanding force may be generated by the self-expanding stent frame whereby the biasing expanding force may be overcome by a tensile force applied generally and at least partially in the direction of the longitudinal axis and comprising a magnitude greater than the biasing force in order to transition or translate the prosthetic heart valve, specifically the valve support, to the second everted position. In this case, when the tensile force is less than the biasing force, the prosthetic heart valve will transition back to the first inverted position.

It is noteworthy that the necessary tensile force to drive the valve support from the everted second position to the inverted first position may come from the biasing expansion force provided by the expanding stent frame, so that as the stent frame expands, either by virtue of shape memory material or by physical means, the valve support is drawn at least partially into the interior of the stent frame and, therefore, into the inverted first position for deployment by the expansion and/or tensile forces generated by the expanding stent.

In other embodiments, the valve support may not comprise a bias toward either the first inverted or the second everted position, but instead is translatable along the longitudinal axis by application of force. The required force in this embodiment may be provided by an operator with push or pull wires that are inserted during the delivery process. Alternatively, the required force in this embodiment, in particular for the translation of the valve support from the second everted position to the first inverted position may be provided by the expanding deployment of the stent frame itself when released from the delivery catheter lumen. In this case, the expanding stent frame, in operative connection with the valve support and as discussed above, will draw the valve support from the second everted position into the first inverted position to achieve full deployment within the heart chamber as a result of tensile forces and/or expansion forces generated by the expanding stent frame.

In all cases, the prosthetic valve comprising the stent frame, valve support and one-way valve within the valve support, are configured to be extended or everted into the second everted position. As will now be readily understood, the stent frame in the deployed position may comprise at least two cross-sectional layers taken along a longitudinal axis, a right side wall and a left side wall. Further, the valve support also comprises at least two cross-sectional layers along the longitudinal axis when deployed, i.e., in the first inverted position, a right side wall and a left side wall. Thus, when in the first inverted position, the valve support layers and the stent frame layers overlap with at least four layers of material present where the overlap occurs and along the longitudinal axis. These at least four layers of material create a maximum outer diameter that can make delivery to the subject heart chamber difficult.

When the second everted position is achieved, the stent frame and/or valve support no longer overlap, so that there is no longer an area where at least four layers of material is present along the longitudinal axis, thus reducing the maximum outer diameter accordingly.

The device may be further compressed to bring the stent frame's right and left side walls together and the valve support's right and left side walls together, most preferably along a single plane to provide the most compressive reduction in size in preparation for positioning with a lumen of a delivery catheter.

Therefore, in certain embodiments, the deployed first inverted position of the prosthetic heart valve may comprise four cross-sectional layers of material where the stent frame and valve support overlap: (1) the left side of stent frame; (2) the right side of stent frame; (3) the left side of the valve support; and (4) the right side of the valve support. Achieving the second everted position removes the valve support from the interior of the stent frame and when compressed as described above reduces the number of cross-sectional layers for the prosthetic heart valve.

In some embodiments, the overall length of the prosthetic heart valve may be temporarily increased in the everted second position, compared with the length in the first inverted position, during translation through the delivery catheter, but the cross-sectional maximum diameter of the device in the everted second position may also be lessened as compared with the cross-sectional diameter of the device when in the inverted first position.

The extension of the prosthetic valve to the second everted position may occur just before loading into the proximal end of the delivery catheter lumen for easier delivery to the heart chamber of interest, e.g., the left atrium. Once the prosthetic valve exits the distal end of the delivery catheter lumen, the prosthetic valve moves, or is moved, from the second everted position to the deployed and first inverted position. As discussed above, this deployment transformation may occur automatically by virtue of biasing or other forces as the stent frame expands.

With reference to the Figures, a variety of prosthetic heart valve device embodiments are illustrated as deployed within an exemplary left atrium, anchored over the annulus 202 and wherein the valve support 104 and/or one-way valve 106 therein is/are disposed above the upper annular surface 200. In each embodiment, the one-way valve 106 and valve support 104 do not physically interact with the native mitral valve leaflets 204, though in other embodiments the valve support and/or one-way valve may physically interact with the native mitral valve leaflets 204.

FIG. 1 provides a prosthetic heart valve device 100 with an exemplary cone-shaped valve support 104. FIG. 2 illustrates a prosthetic heart valve device 100 with an exemplary cylinder-shaped valve support 104. FIG. 3 illustrates a prosthetic heart valve device 100 with an exemplary tapered curvilinear valve support 104, while FIG. 4 shows a prosthetic heart valve device 100 comprising a valve support 104 formed from the stent frame 102 material and turned inside the stent frame 102. FIG. 4 illustrates a valve support 104 defined by an inversion of the stent frame 102. In each embodiment shown, the valve support 104 may be separately manufactured and attached to the stent frame 102 or the valve support 104 may be formed from the stent frame 102. In all cases, the valve support 104 is at least partially disposed within the interior of the stent frame 102, wherein at least a portion of the valve support 104 overlaps with a portion of the stent frame 102 in the overlap region as shown.

FIG. 5A illustrates the prosthetic valve of FIG. 4 in the first inverted position wherein the valve support 104 is at least partially inside the interior of the stent frame 102 and wherein the stent frame 102 and valve support 104 are at least partially overlapping each other, creating a number of material layers in the overlap region. In the illustrated case, there are six layers of overlapping material as indicated by the numbers 1-6 in FIG. 5A. As shown, force may be applied, either by pushing or pulling or a combination of push/pull to transition the device 100 to the second everted position of FIG. 5B which may then be configured and inserted into the lumen 220 of delivery catheter 222 as shown in FIG. 5C for translation therethrough to the distal end of the delivery catheter and release into the subject heart chamber. A primary advantage of the present invention is the reduction of layers of material by eliminating the overlap region as shown in the transition between FIGS. 4A and 5B. In FIG. 5B, only two of the original six layers are present, greatly increasing the opportunity to deliver the device 100 in a form with a smaller maximum diameter as compared with the device of FIG. 5A.

Once released from the delivery catheter lumen 220, the device 100 may be transitioned from the second everted configuration of FIGS. 5C and 5D to the first inverted position of FIGS. 5A and 5E for subsequent positioning and anchoring within the heart chamber.

The length L of the device in the first inverted position may be less than the length L' of the device in the second everted position. Moreover, the diameter D of the device 100 in the first inverted position may be greater than the diameter D' of the device 100 in the second everted position.

The embodiments of FIGS. 1-3 each comprise four layers of material within the overlap region in the first inverted position along longitudinal axis A, but when transitioned to the second everted position, the cross-sectional layers of material are reduced to two, similar to that shown in FIG. 5B.

Various methods are possible using the above-described embodiments.

For example, a method of manipulating the shape of a prosthetic heart valve is possible, the method comprising:

providing a prosthetic heart valve according to this disclosure, the prosthetic heart valve comprising the self-expandable stent frame configured to generate a biasing expanding force, wherein the prosthetic heart valve is in the second everted position;

transitioning the prosthetic heart valve from the second everted position to the first inverted position using at least the biasing expanding force generated by the self-expandable stent frame.

Further, a method of delivering a prosthetic heart valve to a patient's heart chamber using the inventive prosthetic heart valve, comprising:

providing a prosthetic heart valve according to this disclosure, the prosthetic heart valve in the first inverted position;

providing a delivery catheter with a proximal end, a distal end and a lumen therethrough;

positioning the delivery catheter with the distal end within the heart chamber and the proximal end outside of the patient;

transitioning the prosthetic heart valve from the first inverted position to the second everted position;

inserting the prosthetic heart valve in the second everted position into the lumen of the delivery catheter at the proximal end;

translating the prosthetic heart valve through the lumen to the distal end of the delivery catheter;

releasing the prosthetic heart valve from the distal end of the delivery catheter; and transitioning the prosthetic heart valve from the second everted position to the first inverted position within the heart chamber.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

I claim:

1. A prosthetic heart valve for delivery to and implantation within a heart chamber comprising:
    a self-expandable, non-braided, stent frame comprising stent cells and an interior;
    a valve support defined by an inversion of a continuous layer of material formed by the stent cells of the expandable stent frame, wherein the valve support is at least partially disposed in the interior of the stent frame; and
    a one-way valve supported within the valve support, the one-way valve configured to allow blood flow in a forward direction and prevent regurgitation through the one-way valve in a backward direction; wherein the prosthetic heart valve configured to transition between:
a first inverted position wherein the valve support is positioned at least partially within the interior of the stent frame; and
a second everted position wherein the valve support is positioned outside of the stent frame in the downstream direction.

2. The prosthetic heart valve of claim 1, wherein the first inverted position comprises a deployed configuration and the second everted position comprises a delivery configuration.

3. The prosthetic heart valve of claim 2, wherein the self-expandable stent frame is configured to generate an expanding biasing force.

4. The prosthetic heart valve of claim 3, wherein when the prosthetic heart valve is in the second everted position, the expanding biasing force generated by the self-expandable stent frame is alone sufficient to at least partially transition the prosthetic heart valve from the second everted position to the first inverted position.

5. The prosthetic heart valve of claim 3, wherein when the prosthetic heart valve is in the second everted position, the expanding biasing force generated by the self-expandable stent frame in combination with an externally applied force is sufficient to transition the prosthetic heart valve from the second everted position to the first inverted position.

6. The prosthetic heart valve of claim 3, wherein externally applied force is required to transition the prosthetic heart valve from the first inverted position to the second everted position.

7. The prosthetic heart valve of claim 3, wherein when the prosthetic heart valve is in the first inverted position, an externally applied force is required to transition the prosthetic heart valve from the first inverted position to the second everted position.

8. The prosthetic heart valve of claim 1, wherein the prosthetic heart valve in the second everted position comprises a length that is greater than a length of the prosthetic heart valve in the first inverted position.

9. The prosthetic heart valve of claim 8, wherein the prosthetic heart valve in the second everted position comprises a maximum diameter that is smaller than a maximum diameter of the prosthetic heart valve in the first everted position.

10. The prosthetic heart valve of claim 1, wherein the prosthetic heart valve in the second everted position comprises a maximum diameter that is smaller than a maximum diameter of the prosthetic heart valve in the first everted position.

11. The prosthetic heart valve of claim 8, wherein the prosthetic heart valve in the second everted position is further compressible to fit within a lumen of a delivery catheter.

12. The prosthetic heart valve of claim 1, wherein:
the prosthetic heart valve in the first inverted position comprises a number of layers of material along a longitudinal cross-section of the prosthetic heart valve;
the prosthetic heart valve in the second everted position comprises a number of layers of material along a longitudinal cross-section of the prosthetic heart valve; and
the number of layers of material in the second everted position is less than the number of layers in the first everted position.

13. The prosthetic heart valve of claim 12, further comprising two layers of material along the longitudinal cross-section of the prosthetic heart valve in the second everted position.

14. The prosthetic heart valve of claim 1, wherein the prosthetic heart valve is configured to be delivered via a delivery catheter to the heart chamber using a transcatheter access and delivery technique.

15. The prosthetic heart valve of claim 1, wherein the prosthetic heart valve is configured to be delivered via a delivery catheter to the heart chamber using a transcatheter access and delivery technique selected from the group consisting of: transfemoral, transapical, transseptal, transapical and transatrial.

16. The prosthetic heart valve of claim 1, wherein the prosthetic heart valve is configured to be delivered by surgical implantation.

17. The prosthetic heart valve of claim 1, wherein the prosthetic heart valve is configured to at least one of supplement and replace the function of native valve leaflets from the group consisting of: native mitral valve leaflets, native tricuspid valve leaflets, native aortic valve leaflets, and native pulmonary valve leaflets.

18. The prosthetic heart valve of claim 17, wherein when the prosthetic heart valve is in the first inverted configuration and implanted in the heart chamber, the implanted prosthetic heart valve does not physically interact with the native valve leaflets.

19. The prosthetic heart valve of claim 17, wherein when the prosthetic heart valve is in the first inverted configuration and implanted in the heart chamber, the implanted prosthetic heart valve does physically interact with the native valve leaflets.

20. A prosthetic heart valve for implantation in the left atrium of a patient, with at least partial anchoring on the upper annular surface of the left atrium, for at least one of supplementation and replacement of the function of the patient's native mitral valve, the prosthetic heart valve comprising:
a self-expandable, non-braided, stent frame comprising stent cells and an interior;
a valve support defined by an inversion of a continuous layer of material forming the stent cells of the expandable stent frame, wherein the valve support is at least partially disposed in the interior of the stent frame; and
a one-way valve supported within the valve support, the one-way valve configured to allow blood flow in a downstream direction and prevent regurgitation through the one-way valve in an upstream direction, the prosthetic heart valve configured to transition between:
a first inverted deployed position wherein the valve support is positioned at least partially within the interior of the stent frame; and
a second everted delivery position wherein the valve support is positioned outside of the stent frame in the downstream direction; wherein:
when the prosthetic heart valve is implanted within the left atrium, the one-way valve is positioned in one of the locations in the group consisting of: collinear with the upper annular surface, below the upper annular surface, or above the upper annular surface.

21. A method of manipulating a shape of a prosthetic heart valve, the method comprising:
providing a prosthetic heart valve according to claim 1, wherein the self-expandable stent frame is configured to generate a biasing expanding force, wherein the providing is performed when the prosthetic heart valve is in the second everted position; and transitioning the prosthetic heart valve from the second everted position to the first inverted position using at least the biasing expanding force generated by the self-expandable stent frame.

22. The method of claim 21, wherein the prosthetic heart valve has a length in the second everted position that is less than a length of the prosthetic heart valve in the first everted position.

23. A method of delivering a prosthetic heart valve to a patient's heart chamber, the method comprising
providing a prosthetic heart valve according to claim 1 in the first inverted position;
providing a delivery catheter with a proximal end, a distal end and a lumen therethrough;
positioning the delivery catheter with the distal end within the heart chamber and the proximal end outside of the patient;
transitioning the prosthetic heart valve from the first inverted position to the second everted position;
inserting the prosthetic heart valve in the second everted position into the lumen of the delivery catheter at the proximal end;
translating the prosthetic heart valve through the lumen to the distal end of the delivery catheter;
releasing the prosthetic heart valve from the distal end of the delivery catheter; and
transitioning the prosthetic heart valve from the second everted position to the first inverted position within the heart chamber.

\* \* \* \* \*

UNITED STATES PATENT AND TRADEMARK OFFICE
CERTIFICATE OF CORRECTION

PATENT NO. : 12,036,113 B2
APPLICATION NO. : 16/007630
DATED : July 16, 2024
INVENTOR(S) : Saravana B. Kumar Page 1 of 1

It is certified that error appears in the above-identified patent and that said Letters Patent is hereby corrected as shown below:

In the Specification

Column 2, Line 44, replace "second inverted position" with --second everted position--;
Column 2, Line 45, replace "second inverted position" with --second everted position--.

Signed and Sealed this
Eighth Day of April, 2025

Coke Morgan Stewart
*Acting Director of the United States Patent and Trademark Office*